United States Patent
Hynes

(10) Patent No.: US 11,278,372 B2
(45) Date of Patent: Mar. 22, 2022

(54) SURGICAL STERILIZATION SYSTEM AND METHOD

(71) Applicant: Warsaw Orthopedic, Inc, Warsaw, IN (US)

(72) Inventor: Richard A. Hynes, Melbourne Beach, FL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 667 days.

(21) Appl. No.: 15/923,973

(22) Filed: Mar. 16, 2018

(65) Prior Publication Data

US 2019/0282329 A1 Sep. 19, 2019

(51) Int. Cl.

| A61B 90/80 | (2016.01) |
|---|---|
| A61F 13/40 | (2006.01) |
| A61L 2/00 | (2006.01) |
| A61B 46/20 | (2016.01) |
| A61G 13/10 | (2006.01) |

(52) U.S. Cl.
CPC .............. *A61B 90/80* (2016.02); *A61B 46/20* (2016.02); *A61G 13/10* (2013.01); *A61L 2/0088* (2013.01); *A61M 35/006* (2013.01)

(58) Field of Classification Search
CPC .............................. A61M 35/006; A61B 90/80
See application file for complete search history.

(56) References Cited

U.S. PATENT DOCUMENTS

| 4,507,111 | A | 3/1985 | Gordon et al. |
|---|---|---|---|
| 8,740,488 | B2 | 6/2014 | Cable et al. |
| 2005/0096748 | A1* | 5/2005 | Yoon ...................... A61B 17/56 623/22.4 |
| 2005/0279364 | A1* | 12/2005 | Vrzalik .................. A61G 13/00 128/845 |
| 2006/0137693 | A1* | 6/2006 | Lewis ..................... A61B 46/00 128/849 |
| 2015/0313683 | A1 | 11/2015 | Kowalewski et al. |
| 2016/0270772 | A1* | 9/2016 | Beale ............... A61B 17/00234 |
| 2017/0367783 | A1* | 12/2017 | Taylor .............. A61B 5/150022 |

OTHER PUBLICATIONS

Boissiere et al. Lumbar-sacral fusion by a combined approach using interbody PEEK cage and posterior pedicle-screw fixation: Clinical and radiological results from a prospective study. Orthopaedics & Traumatology: Surgery & Research vol. 99, Issue 8, Dec. 2013, pp. 945-951 (Year: 2013).*

Barrey et al. One-stage combined lumbo-sacral fusion, by anterior then posterior approach: clinical and radiological results. Eur Spine J. Nov. 2013; 22(Suppl 6): 957-964. (Year: 2013).*

* cited by examiner

*Primary Examiner* — Donald R Spamer
(74) *Attorney, Agent, or Firm* — Sorell, Lenna & Schmidt, LLP

(57) ABSTRACT

A method of preparing a surgical site includes the steps of: disposing a preparation material with a selected surface of a patient body, the selected surface includes a sterile region having a boundary; engaging a first applicator with the selected surface and moving the first applicator along a path from a first incision site of the selected surface to the boundary; engaging a second surgical applicator with the selected surface and moving the second applicator along a path from a second incision site of the selected surface to the boundary, the path of the first applicator intersecting the path of the second applicator. In some embodiments, surgical systems and surgical instruments are disclosed.

16 Claims, 9 Drawing Sheets

SURGICAL STERILIZATION SYSTEM AND METHOD

TECHNICAL FIELD

The present disclosure generally relates to medical devices for the treatment of musculoskeletal disorders, and more particularly to a surgical sterilization system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders can include correction, fusion, fixation, discectomy, laminectomy and implantable prosthetics. As part of these surgical treatments, spinal implants including spinal constructs and interbody devices are often used to restore proper alignment and generally support the vertebral members. During surgical treatment, a surgical site including, for example, a patient surface can be sterilized via agents such as medicines, fluids, antiseptics or gels. This disclosure describes an improvement over these prior technologies.

SUMMARY

In one embodiment, a method of preparing a surgical site is provided. The method includes the steps of: disposing a preparation material with a selected surface of a patient body, the selected surface includes a sterile region having a boundary; engaging a first applicator with the selected surface and moving the first applicator along a path from a first incision site of the selected surface to the boundary; engaging a second surgical applicator with the selected surface and moving the second applicator along a path from a second incision site of the selected surface to the boundary, the path of the first applicator intersecting the path of the second applicator. In some embodiments, surgical systems and surgical instruments are disclosed.

In one embodiment, a method of preparing a surgical site includes the steps of: applying an antiseptic fluid to a selected surface of a patient body, the selected surface including a sterile region having a boundary; engaging a first applicator with a center of a first incision and moving the first applicator in a continuous spiral configuration along a first path to the boundary; and engaging a second applicator with a center of a second incision and moving the second applicator in a continuous spiral configuration along a second path to the boundary, the path of the first applicator intersecting the path of the second applicator.

In one embodiment, a method of preparing a surgical site includes the steps of: positioning a patient body right side down in a lateral decubitus position; disposing a preparation material with a selected surface of the patient body, the selected surface including a sterile region having a boundary; engaging a first applicator with the selected surface and moving the first applicator along a path from a center of an anterior incision of the selected surface to the boundary; and engaging a second applicator with the selected surface and moving the second applicator along a path from a center of a posterior incision of the selected surface to the boundary, the paths intersect at one half a distance between the respective centers of the incisions.

BRIEF DESCRIPTION OF THE DRAWINGS

The present disclosure will become more readily apparent from the specific description accompanied by the following drawings, in which.

DETAILED DESCRIPTION

Figure 1:
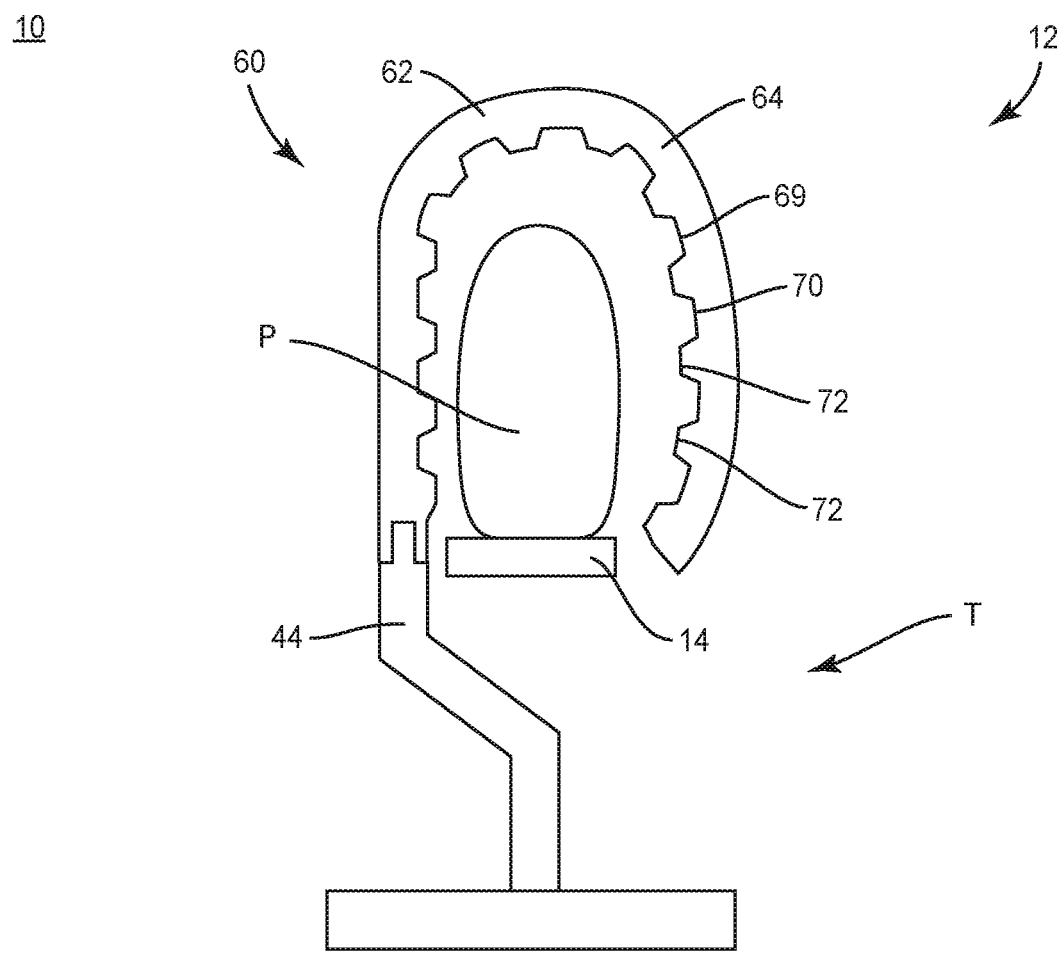
FIG. 1 is a plan view, in cross section, of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical sterilization system and method for treating a spine. In some embodiments, the systems and methods of the present disclosure comprise medical devices that establish and maintain a sterile surgical field with a patient and are employed with a surgical treatment of a cervical, thoracic, lumbar and/or sacral region of a spine. In some embodiments, the present disclosure includes a sterilization system disposed about a patient and employed with a surgical table.

In some embodiments, the present sterilization system and method is employed with a surgical draping system disposed about a patient and employed with a surgical table such that the patient can be rotated intra-operatively while maintaining a sterile surgical field. See also, the examples and disclosure of a surgical drape system and methods shown and described in commonly owned and assigned U.S. patent application Ser. No. 15/923,883 filed Mar. 16, 2018, and published as U.S. Patent Application Publication No.

2019028316, on Sep. 19, 2019; and U.S. patent application Ser. No. 15/923,944 filed Mar. 16, 2018, and published as U.S. Patent Application Publication No. 2019028317, on Sep. 19, 2019, the entire contents of each of these disclosures being incorporated herein by reference.

In some embodiments, the present surgical sterilization system comprises a sterilization member connected with a surgical table. In some embodiments, a patient is disposed with the surgical table. In some embodiments, the sterilization member is connected with a vertical member that is attached with the surgical table. In some embodiments, the vertical member is attached with a base of the surgical table at a junction. In some embodiments, the sterilization member includes a sterilization loop. In some embodiments, the sterilization loop is configured for attachment with the vertical member. In some embodiments, the sterilization loop includes a patient-facing surface. In some embodiments, one or a plurality of nozzles are distributed evenly along the patient-facing surface. In some embodiments, the nozzles are configured to spray streams of antiseptic fluid on the patient. See also, the examples and disclosure of surgical sterilization systems shown and described in commonly owned and assigned U.S. patent application Ser. No. 15/924,021 filed Mar. 16, 2018, and published as U.S. Patent Application Publication No. 20190282330, on Sep. 19, 2019; the entire contents of which being incorporated herein by reference.

In some embodiments, the present surgical sterilization system includes a method of preparing a surgical site. In some embodiments, the method includes the step of positioning a patient right side down in a lateral decubitus position, In some embodiments, the patient is positioned such that only the torso is accessible. In some embodiments, an applicator, such as, for example, a sterile sponge is utilized to apply antiseptic fluid at a location of an incision, such as, for example, a posterior incision. In some embodiments, the sterile sponge follows a path from the incision to the border of a sterile field. In some embodiments, the path includes starting from the incision and moving outward in a circular motion. In some embodiments, the circular motion includes making larger and larger circles in a spiral. In some embodiments, an applicator, such as, for example, a sterile sponge follows a path starting from an incision, such as, for example, an anterior incision, In some embodiments, a second path meets a first path on a lateral portion of the torso.

In some embodiments, the present surgical sterilization system is employed with a method of preparing a surgical site and used with a surgical drape for angular rotation of a patient during spine surgery. In some embodiments, the present surgical sterilization system is employed with a method of preparing a surgical site and used with a telescoping surgical drape. In some embodiments, the present surgical sterilization system is employed with a method of preparing a surgical site and used with an adhesive sterile tube drape for use with a single pedestal surgical table.

In some embodiments, the present surgical sterilization system includes a sterilization member connected with a rail-mounted applicator of a surgical table and applies an agent to a surface of a patient. In some embodiments, the present surgical sterilization system is employed with a single-post surgical table. In some embodiments, the present surgical sterilization system is employed with a surgical table such that a patient is rotatable in a range of 0 through 360 degrees without breaking sterility. In some embodiments, the present surgical sterilization system includes a surgical drape that can be applied circumferentially around a patient to maintain a sterile field while the patient is rotated 360 degrees intra-operatively via a surgical table. In some embodiments, the present surgical sterilization system is employed with a surgical drape that can be employed with spinal procedures including a rotating surgical table such that surgeons can access any part of a spine from different aspects of the patient. In some embodiments, the surgical drape is movable between a non-deployed orientation and a deployed orientation.

In some embodiments, the present surgical sterilization system is employed with a surgical table having a single post supporting the table. In some embodiments, the surgical drape includes one or more sterilization loops that move along a length of the surgical table. In some embodiments, the sterilization loop can have alternate configurations, such as, for example, circular, oval, triangle or rectangular. In some embodiments, the sterilization loop is disposed about at least a portion of a patient circumferentially. In some embodiments, the sterilization loop includes one or more loops that slide along a rail.

In some embodiments, the present surgical sterilization system is employed with a surgical drape including a deployment loop and draping that is deployed circumferentially using the deployment loop. In some embodiments, the draping is deployed in a 360 degree configuration about the patient. In some embodiments, the draping is attached to the deployment loop. In some embodiments, the draping includes a sterile adhesive drape tube mounted with a deployment loop. In some embodiments, the deployment loop is configured for disposal about a patient. In some embodiments, the deployment loop is connected to a bottom rail of a surgical table. In some embodiments, the surgical drape includes a deployment loop slidable in a cranial direction and a deployment loop slidable in a caudal direction. In some embodiments, the surgical drape includes a first deployment loop and a second deployment loop such that the deployment loops are individually and/or separately slidable in a cranial direction and/or a caudal direction from a mid-section of a patient. In some embodiments, the surgical drape includes one or more deployment loops that are slidable via automated movement and/or manual movement via a sterile operator.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone, lateral or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and iliac regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system and related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system 10.

The components of surgical system 10 can be fabricated from biologically acceptable materials suitable for medical applications. For example, the components of surgical system 10, individually or collectively, can be fabricated from materials such as super-elastic titanium alloys, superelastic metallic alloys (e.g., Nitinol, super elasto-plastic metals, such as GUM METAL®), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene or epoxy.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 may be employed, for example, with minimally invasive procedures, including percutaneous techniques, mini-open surgical techniques and/or open surgical techniques to establish and maintain a sterile surgical field with a patient in connection with a surgical treatment of a spine. In some embodiments, the components of surgical system 10 are employed in connection with surgical treatment that includes access to a surgical site by one or a plurality of surgical approaches. For example, the components of surgical system 10 can be employed with spinal procedures that include access during a single procedure and/or simultaneous access to one or a plurality of surgical approaches and/or surgical pathways including one or more incisions within a sterile boundary. In some embodiments, during a surgical procedure, a patient is disposed with a surgical table that can articulate, orient, position, reposition and/or manipulate the patient for alignment with one or a plurality of surgical approaches. The components of surgical system 10 maintain sterility during such movement of the patient within an enclosed surgical field and/or boundary, for example, during angular rotation of a patient for alignment with one or a plurality of surgical approaches, as described herein. The surgical procedure can include surgical treatment of a cervical, thoracic, lumbar and/or sacral region of a spine.

Surgical system 10 includes a surgical sterilization system 12. Surgical sterilization system 12 includes a surgical table T. Surgical table T includes a support 14 configured for disposal of a patient P. Support 14 is configured to maintain patient P in various orientations, such as, for example, supine, prone or on a side. In some embodiments, support 14 is planar. Support 14 extends between an end 16 and an end 18. Surgical table T is supported by a single pedestal 20. Pedestal 20 extends from end 16 of support 14. Positioning of pedestal 20 at end 16 facilitates translation of a sterilization member 60 and/or a surgical draping system 100, as described herein, relative to support 14, by providing free translation and unencumbered passage of a post 44 along support 14. In some embodiments, surgical table T includes a second support configured to facilitate maintaining the position of patient P during rotation of surgical table T.

Figure 2:
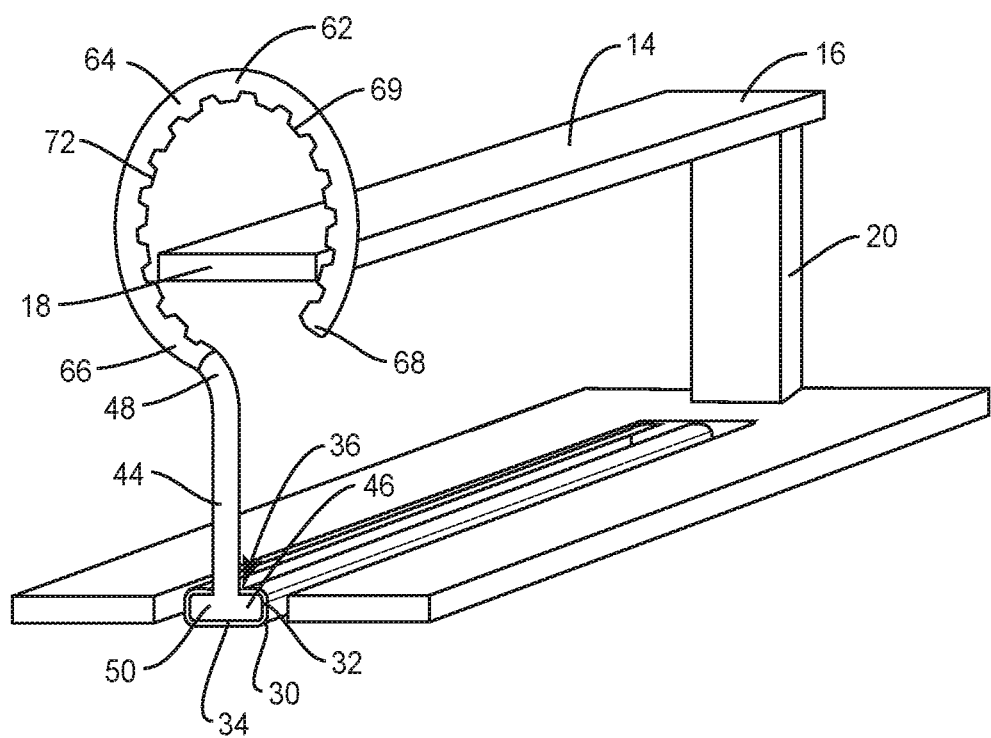
FIG. 2 is a perspective view of components of one embodiment of a surgical system in accordance with the principles of the present disclosure.

Surgical table T includes a base rail 30 that extends from pedestal 20, as shown in FIG. 2. Rail 30 extends along all or a portion of support 14. Rail 30 includes a connecting mechanism for connection of post 44 thereto, as described herein. Rail 30 includes a surface 32 that defines a slot, such as, for example, a track 34. Track 34 is in open communication with surface 32 to define a track pathway 36. Track pathway 36 facilitates translation of sterilization member 60 and/or a surgical draping system 100 relative to patient P, as described herein. In some embodiments, track pathway 36 is linear in shape. In some embodiments, all or only a portion of track pathway 36 may have alternate configurations, such as, for example, arcuate, undulating and/or offset.

Figure 3:
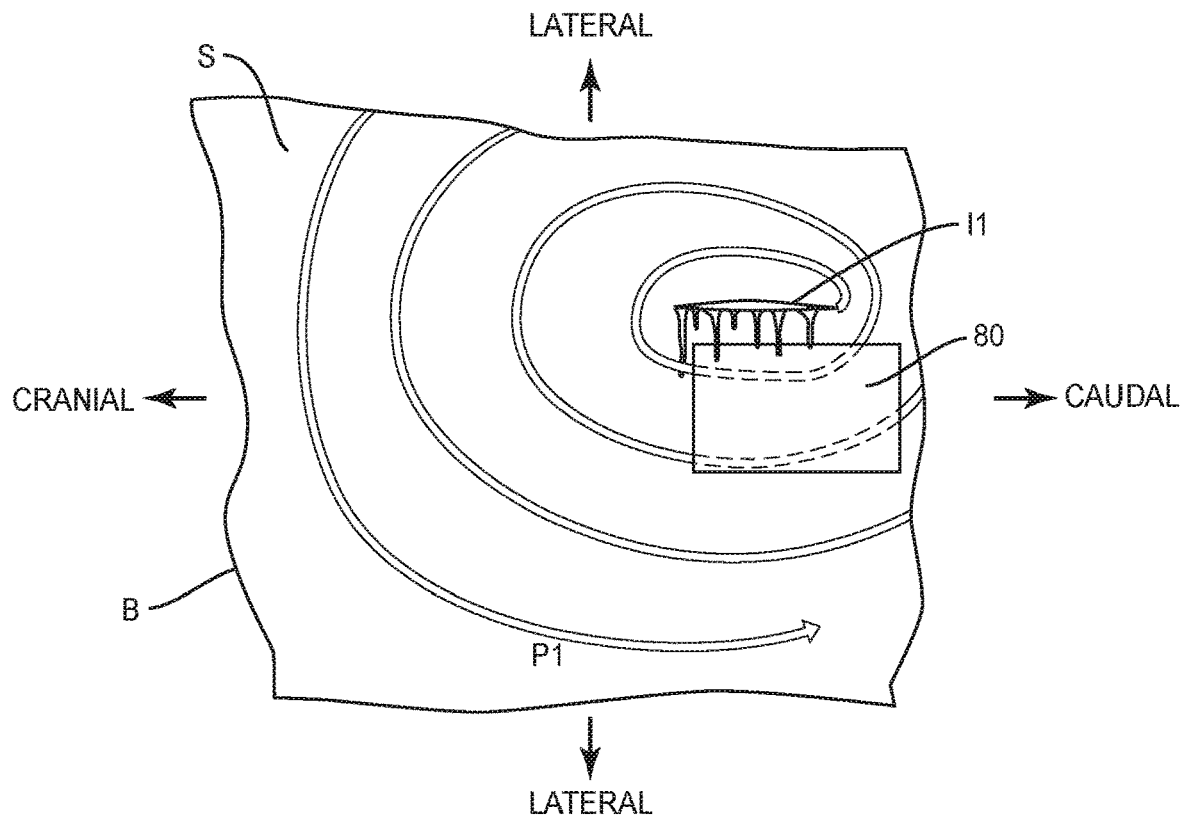
FIG. 3 is a plan view illustrating a method of one embodiment of a surgical system in accordance with the principles of the present disclosure.
Figure 4:
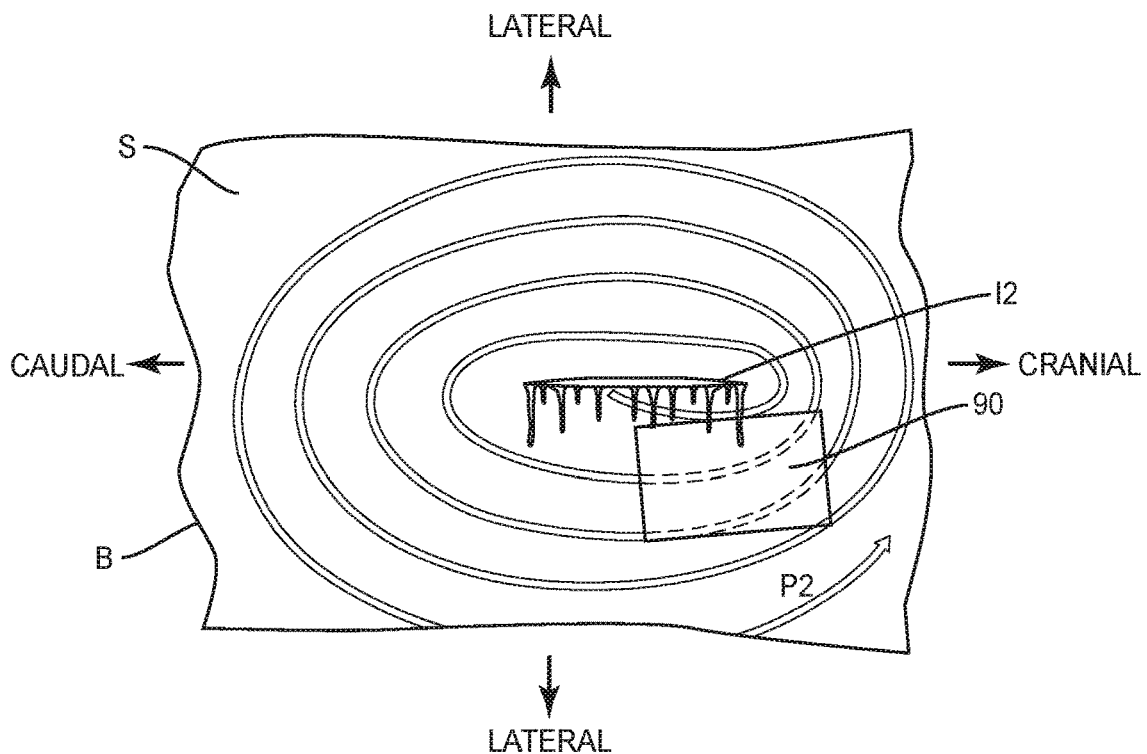
FIG. 4 is a plan view illustrating a method of one embodiment of a surgical system in accordance with the principles of the present disclosure.
Figure 5:
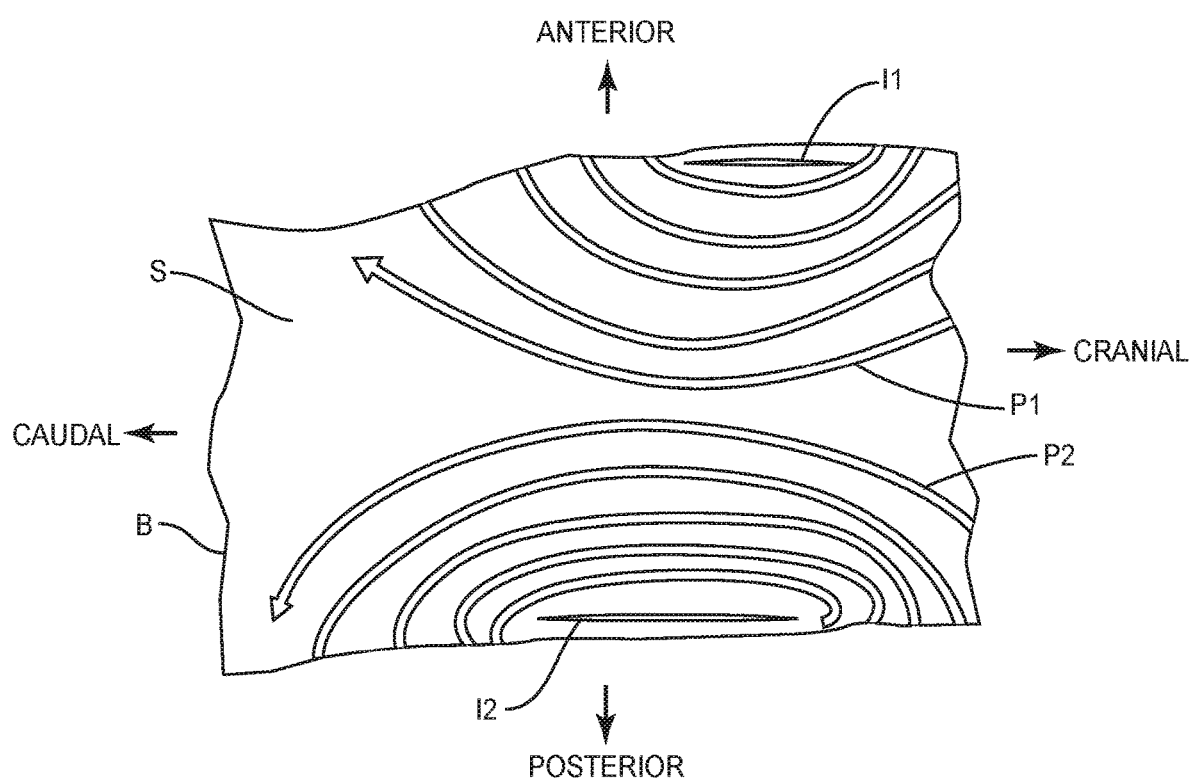
FIG. 5 is a plan view illustrating a method of one embodiment of a surgical system in accordance with the principles of the present disclosure.
Figure 6:
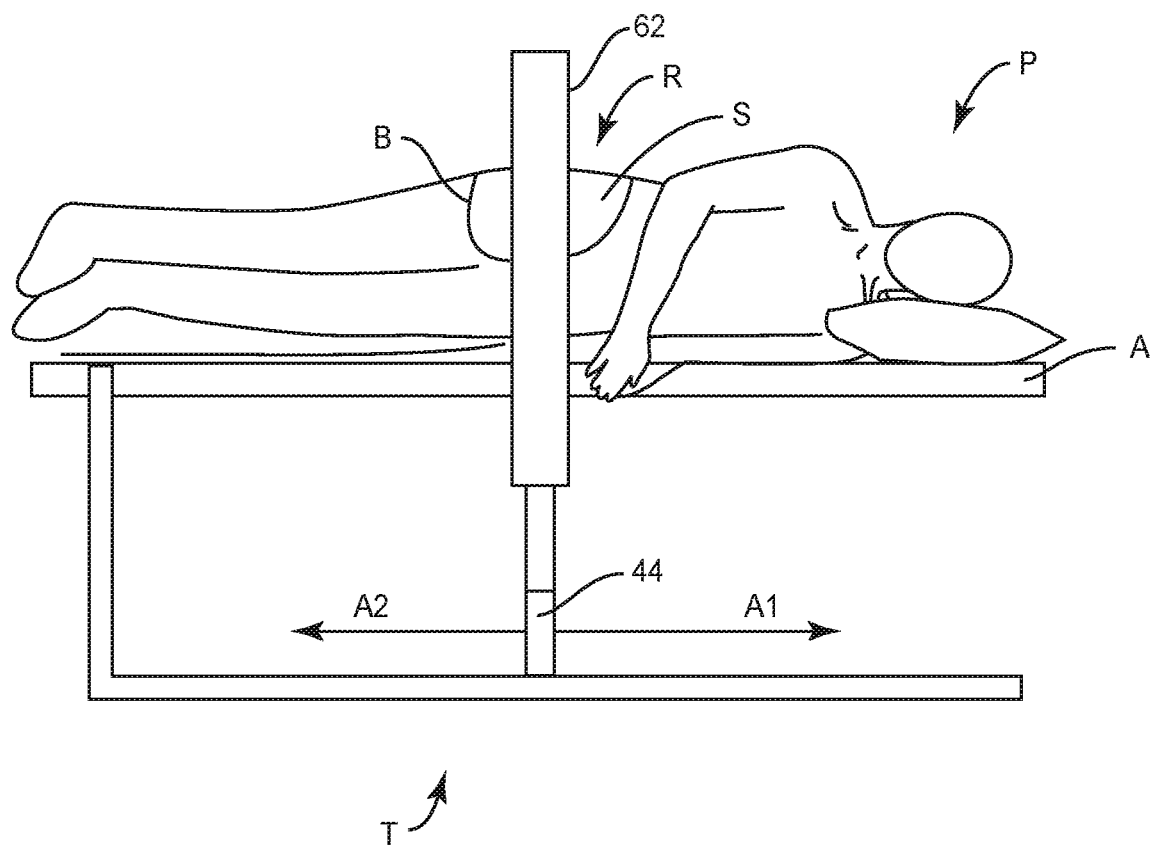
FIG. 6 is a side view of components of one embodiment of a surgical system in accordance with the principles of the present disclosure.

Post 44 extends between an end 46 and an end 48. Post 44 is configured for connection with track 34 via end 46. End 46 includes a T-shaped slider 50 configured to engage track 34. Slider 50 is engageable with track 34 for slidable translation of sterilization member 60 and/or a surgical draping system 100 relative to patient P along track pathway 36. Post 44 is translated along track pathway 36 to align sterilization member 60 relative to a selected surface S of a body of patient P. Selected surface S includes a sterile region R having a boundary B, as shown in FIG. 6. Boundary B is determined by the surgical procedure and/or number and placement of incisions. In some embodiments, a surgical procedure requires two incisions, such as, for example, an anterior incision I1 and a posterior incision I2 disposed within sterile region R and boundary B, as shown in FIGS. 3-5.

Sterilization member 60 includes a sterilization loop 62. Sterilization loop 62 includes an arm 64. Arm 64 extends between an end 66 and an end 68. Post 44 is connectable with end 66 of arm 64, as shown in FIG. 2. In some embodiments, post 44 is connected with end 66, such as, for example, with clips, hooks, adhesives and/or flanges. In some embodiments, post 44 and arm 64 are monolithically formed. In some embodiments, post 44 is a separate component from arm 64. In some embodiments, post 44 is an integral component with arm 64.

Arm 64 includes an arcuate configuration to facilitate orienting and/or manipulating sterilization member 60 about patient P. Arm 64 disposes sterilization member 60 circumferentially about a portion of patient P. Arm 64 includes a surface 69 configured and oriented to face a surface S of patient P. In some embodiments, arm 64 includes a hook configuration. In some embodiments, arm 64 includes a circular configuration. In some embodiments, sterilization loop 62 includes one or more relatively moveable arms 64, which can be connected, for example, by one or more hinges. In some embodiments, arm 64 is flexible and is movable and/or malleable to a plurality of orientations to conform to a shape of patient P. In some embodiments, sterilization member 60 is disposed about all or only a portion of patient P.

Sterilization member 60 includes a dispenser 70 connected with sterilization loop 62. In some embodiments, dispenser 70 includes one or a plurality of nozzles 72. Nozzles 72 are uniformly disposed along surface 69 to facilitate application of antiseptic fluid AF on a surgical site, for example, including surface S. In some embodiments, nozzles 72 are selectively oriented and aligned with a surgical site, for example, including surface S to apply, disperse, coat, layer, dispose, spread and/or adhere an agent in a selected configuration, pattern and/or orientation with surface S. In some embodiments, nozzles 72 are disposed at alternate orientations along surface 69. Each nozzle 72 includes an opening disposed in communication with surface 69. Each nozzle 72 includes a hose portion (not shown) connectable to a fluid source of a surgical preparation and/or sterilization agent, such as, for example, antiseptic fluid AF.

In some embodiments, the agent may include, such as, for example, iodine, an iodine complex, chlorhexidine, chlorhexidine salts, alcohol, or combinations thereof. In some embodiments, iodine complexes may include iodophors, e.g., povidone-iodine USP. In some embodiments, chlorhexidine salts may include, e.g., chlorhexidine digluconate, chlorhexidine diacetate. In some embodiments, the agent can include antimicrobial agents such as C2-C5 lower alkyl alcohols (including, e.g., ethyl alcohol, 1-propanol, and 2-propanol), parachlorometaxylenol (PCMX), triclosan, hexachlorophene, fatty acid monoesters of glycerin and propylene glycol such as glycerol monolaurate, glycerol monocaprylate, glycerol monocaprate, propylene glycol monolaurate, propylene glycol monocaprylate, propylene glycol moncaprate, phenols, surfactants, and polymers that include a (C12-C22) hydrophobe and a quaternary ammonium group, polyquaternary amines such as polyhexamethylene biguanide, quaternary ammonium silanes, silver, silver salts (such as silver chloride), silver oxide and silver sulfadiazine, methyl, ethyl, propyl and butyl parabens, octenidene or peroxides (e.g., hydrogen peroxide and benzoyl peroxide).

Nozzles 72 are configured to allow the passage of antiseptic fluid AF therethrough. Nozzles 72 spray, direct and/or modify a flow of antiseptic fluid AF through nozzles 72 about surface S of patient P. In some embodiments, nozzles 72 may be used to control a selected rate of flow, speed, direction, mass, shape and/or pressure of a stream of antiseptic fluid AF. In some embodiments, nozzles 72 include various configurations to alter a desired rate of flow and/or a droplet size based on a size of surface S and desired sterile region R. In some embodiments, nozzle 72 forms a flow of antiseptic fluid AF, such as, for example, a concentrated jet or a dispersed jet. In some embodiments, the flow of antiseptic fluid AF may be in a range of 4 to 15 pounds per square inch. In some embodiments, nozzle 72 is configured to form a droplet size in the range of 200-500 microns. In some embodiments, nozzles 72 can be disposed with loop 62 at various orientations to provide for varied flow of antiseptic fluid AF relative to patient P.

Sterilization member 60 is translatable relative to surface S along track 34. In some embodiments, sterilization member 60 is rotatable relative to surface S. Nozzles 72 via sterilization loop 62 are selectively translatable relative to surface S to facilitate even distribution of antiseptic fluid AF along surface S. In some embodiments, sterilization loop 62 is translated automatically, for example, via processor controlled surgical table machine components, relative to surgical table T for a hands-free sterilization of surface S. In some embodiments, sterilization loop 62 is translatable in a direction, such as, for example, a cephalad direction, as shown by arrow A1 in FIG. 6, and in a direction, such as, for example, a caudal direction, as shown by arrow A2 in FIG. 6. In some embodiments, sterilization member 60 is fixed relative to surgical table T and patient P is moveable relative to sterilization member 60 to align selected surface S with nozzles 72.

Sterilization loop 62 is configured to orient nozzles 72 for circumferential disposal about patient P for a uniform distribution of antiseptic fluid AF about patient P. Antiseptic fluid AF is sprayed from nozzles 72 in the form of fine droplets. The droplets flow from surface 69 to surface S. As such, bacteria floating between surface 69 and surface S is sterilized to define sterile regions R. The droplets stick to surface S thereby wetting surface S for surgical preparation and sterilization.

In some embodiments, surgical sterilization system 12 includes an applicator, such as, for example, a sterile sponge 80, and an applicator, such as, for example, a sterile sponge 90 configured to apply, disperse, coat, layer, dispose, spread and/or adhere antiseptic fluid AF relative to surface 5, as shown in FIGS. 3-5 and described herein. In operation, antiseptic fluid AF is applied to selected surface S, as described herein, and the surgical site is prepared by sponges 80, 90. Sterile sponge 80 is disposed with surface S adjacent a center of a selected site for an incision I1, for example, an anterior incision, with a patient lying right side down in a lateral decubitus position such that a patient torso is shown, as illustrated in FIG. 3. Sponge 80 is moved along a path P1 starting from the center of the selected site for incision I1 to boundary B. Sponge 80 is moved along path P1 in a plurality of outward sweeping motions, such as, for example, swaths. In some embodiments, the swaths increase in dimension from the center of the selected site for incision I1 to boundary B. In some embodiments, the swaths include a continuous spiral configuration. In some embodiments, the swaths include a continuous outward circular motion to boundary B.

Sterile sponge 90 is disposed with selected surface S at a center of a selected site for an incision I2, for example, a posterior incision, with a patient lying right side down in a lateral decubitus position such that a posterior aspect of patient P is shown, as illustrated in FIG. 4. Sponge 90 is moved along a path P2 starting from the center of the selected site for incision I2 to boundary B. Sponge 90 is moved along path P2 in a plurality of swaths that increase in dimension from the center of the selected site for incision I2 to boundary B. In some embodiments, the swaths include a continuous spiral configuration. In some embodiments, the swaths include a continuous outward circular motion to boundary B. With patient P lying right side down in a lateral decubitus position and left side up such that the left side of a patient torso is shown, as illustrated in FIG. 5, path P1 intersects path P2, for example, at one half a distance between the respective centers of the selected sites for incision I1 and incision I2. In some embodiments, path P1 can intersect, cut, cross, overlap and/or divide path P2 at one or a plurality of locations between the respective centers of the selected sites for incision I1 and incision I2. In some embodiments, paths P1, P2 begin at the respective centers of the selected sites for incisions I1, I2 and extend in a circular pattern outward from the respective centers. Sponges 80, 90 are manipulated along paths P1, P2 to resist and/or prevent antiseptic fluid AF from being applied to incisions I1, I2 after sponges 80, 90 are moved from incisions I1, I2.

In assembly, operation and use, as shown in FIGS. 6-12, surgical system 10, similar to the systems and methods described herein, includes sterilization member 60, which is employed in connection with a surgical approach strategy for a surgical procedure to treat one or more spinal disorders.

In connection with one or more selected surgical approaches, for example, the lateral and postero-lateral or posterior surgical approaches, the surgical site, which may include one or more incisions, retracted openings, pathways and/or passageways created with the body of patient P, are identified and/or determined to define sterile region R. For example, sterile region R includes the one or more incisions, retracted openings, pathways and/or passageways aligned with the lateral and postero-lateral or posterior surgical approaches created in the tissue surfaces of patient P disposed within selected surface S, which bounds sterile region R. In some embodiments, sterile region R is established and maintained above a surface of surgical table T. In some embodiments, the space above the surface of surgical table T is considered a sterile region. In some embodiments, the space from surgical table T to the floor is considered a non-sterile region. In some embodiments, the surgical site and/or sterile region R include vertebral tissue. For example, the procedure can include access via a lateral surgical approach and a separate postero-lateral or posterior surgical approach.

Patient P is positioned on surgical table T, for example, in a lateral position. Surgical table T is mechanically configured to rotate, reposition and/or manipulate patient P in connection with a spinal procedure to provide access to one or more selected surgical approaches and/or vertebral tissue at the surgical site. In some embodiments, surgical table T rotates patient P into alignment with the selected surgical approaches via a 360 angular degree rotation of surgical table T about an axis A, as shown in FIG. 6. In some embodiments, one or more practitioners may physically manipulate patient P for rotation to provide simultaneous access to the selected surgical approaches.

Figure 7:
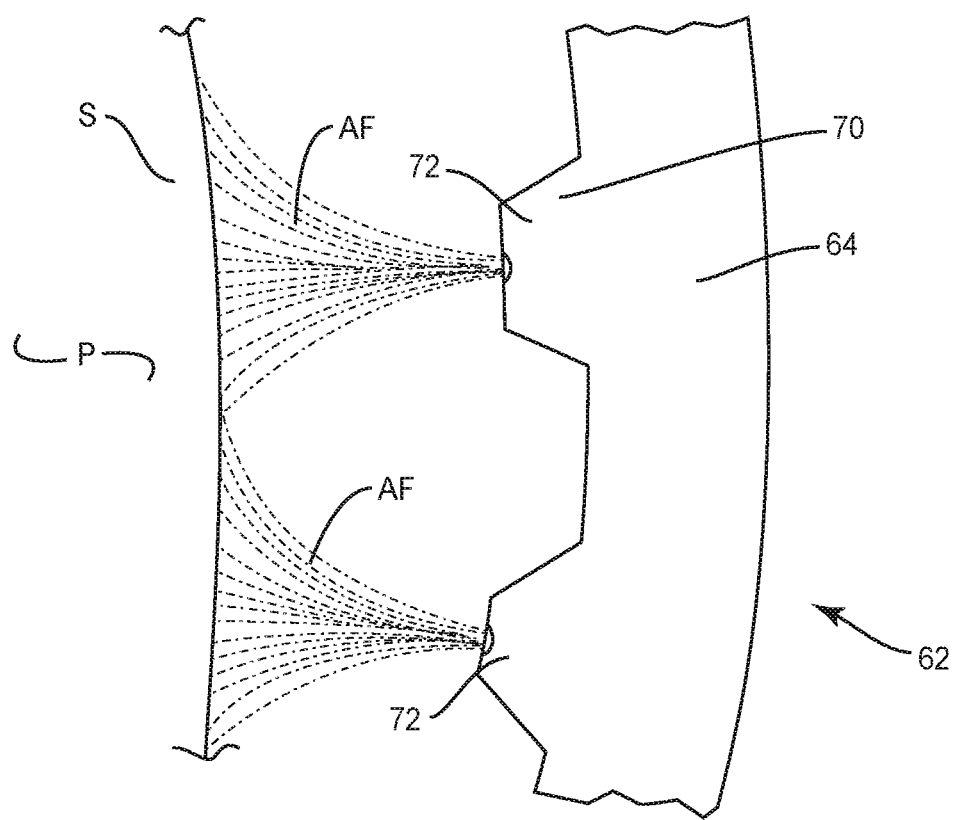
FIG. 7 is a plan view of components of one embodiment of a surgical system in accordance with the principles of the present disclosure.

Patient P is prepared for surgery by sterilizing the surgical site to resist and/or prevent infection from pathogens disposed on skin of patient P. Sterilization loop 62 extends from post 44 and is disposed adjacent a mid-section of patient P. Sterilization loop 62 is disposed to orient nozzles 72 circumferentially about a portion of patient P to sterilize a surgical site to define sterile region R. Nozzles 72 direct a flow of antiseptic fluid AF onto surface S, as shown in FIG. 7 and described herein. Sterilization loop 62 is translatable in a cephalad direction, as shown by arrow A1 in FIG. 6, and/or in a caudal direction, as shown by arrow A2 in FIG. 6, to uniformly distribute antiseptic fluid AF onto surface 5, as described herein.

Fluid AF is applied to surface S and sterile sponge 80 is disposed with surface S at a center of a selected site of an anterior incision I1 with a patient lying right side down in a lateral decubitus position such that a patient torso is shown, as illustrated in FIG. 3. Sponge 80 is moved in a continuous spiral configuration along path P1 starting from the center of the selected site for incision I1 to boundary B. Sponge 80 is moved along path P1 in a plurality of outward sweeping swaths of increasing dimension from the center of the selected site for incision I1 to boundary B.

Sterile sponge 90 is disposed with surface S at a center of a selected site of a posterior incision I2 with a patient lying right side down in a lateral decubitus position such that a posterior aspect of patient P is shown, as illustrated in FIG. 4. Sponge 90 is moved in a continuous spiral configuration along path P2 starting from the center of the selected site for incision I2 to boundary B. Sponge 90 is moved along path P2 in a plurality of outward sweeping swaths of increasing dimension from the center of the selected site for incision I2 to boundary B. With patient P lying right side down in a lateral decubitus position and left side up such that the left side of a patient torso is shown, as illustrated in FIG. 5, path P1 intersects path P2 at one half a distance between the respective centers of the selected sites for incision I1 and incision I2. In some embodiments, paths P1, P2 intersect at a lateral side of a torso of patient P equidistant from the respective centers of the selected sites for incisions I1, I2.

Surface S is sterilized and a surgical drape 212 is positioned with patient P and surgical table T, as shown in FIGS. 8-12. Surgical drape 212 is configured for bi-directional telescopic deployment to enclose patient P and provide access to one or more selected surgical approaches in connection with surgical treatment of a spine. In some embodiments, surgical access can include access and/or repositioning to a right lateral side portion, a left lateral side portion, an anterior portion and/or a posterior portion of patient P. In some embodiments, surgical access can include access to a posterior portion of a patient P and a lateral side of patient P. In some embodiments, surgical access can include access to an anterior portion of patient P and a lateral side of patient P.

Figure 9:
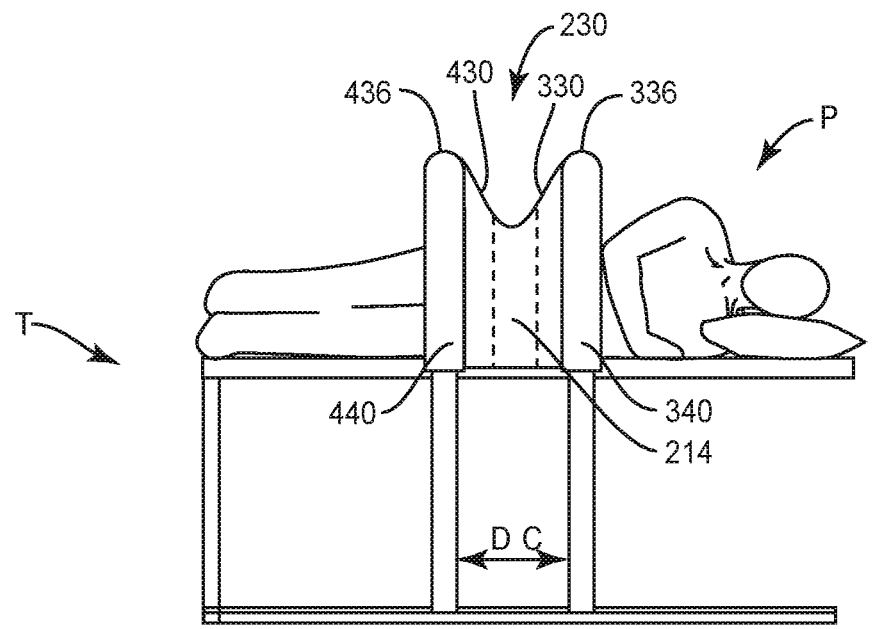
FIG. 9 is a side view of the components shown in FIG. 8.

Surgical drape 212 includes a seal 214 and a draping 230. Seal 214 is configured to adhere to a surface of a body of patient. Seal 214 is connected and/or adhered to the body surface after the initial preparation of the sterile surgical site, as described herein. Draping 230 includes a section 330 and a section 430, as shown in FIG. 9. Section 330 is connected to an end of seal 214. Section 430 is connected to an opposite end of seal 214.

Figure 8:
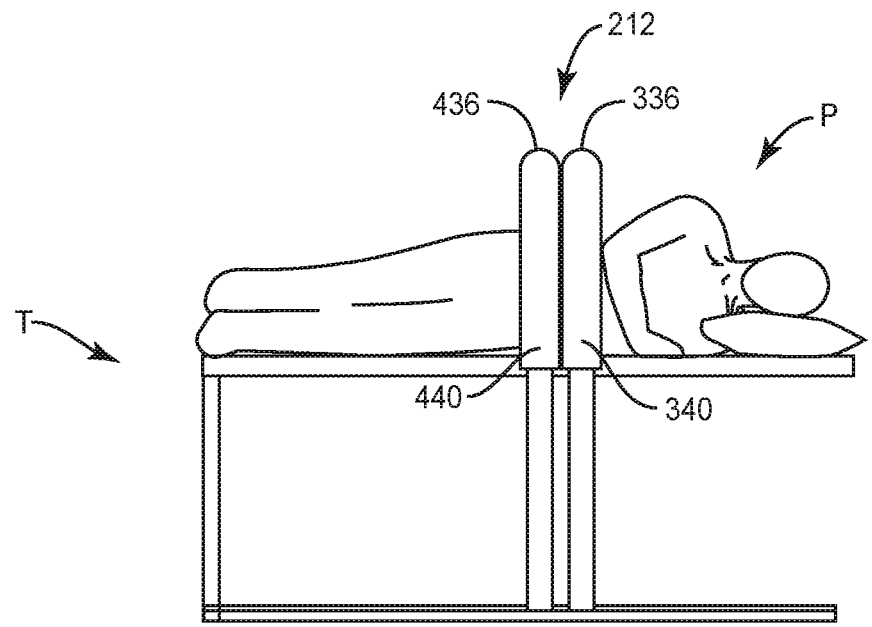
FIG. 8 is a side view of components of one embodiment of a surgical system in accordance with the principles of the present disclosure.
Figure 10:
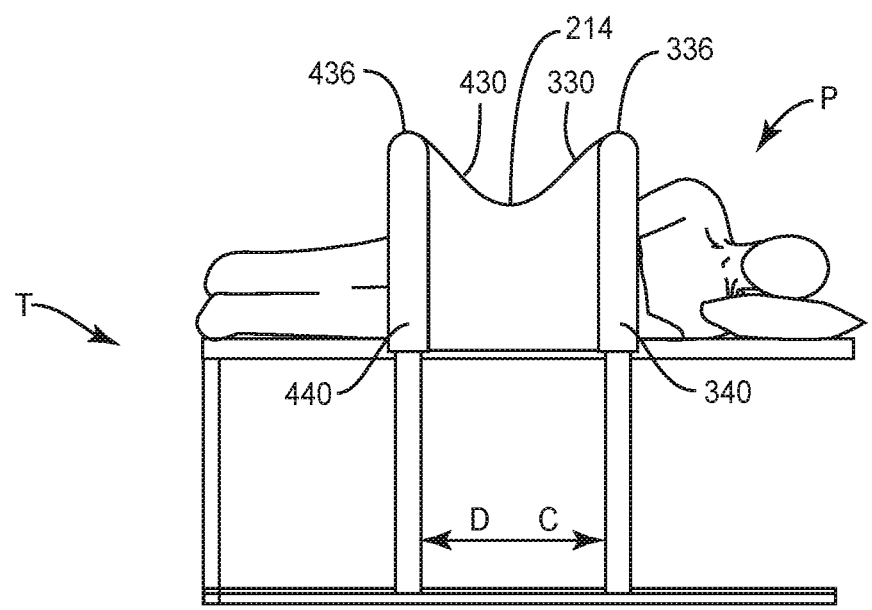
FIG. 10 is a side view of the components shown in FIG. 8.
Figure 11:
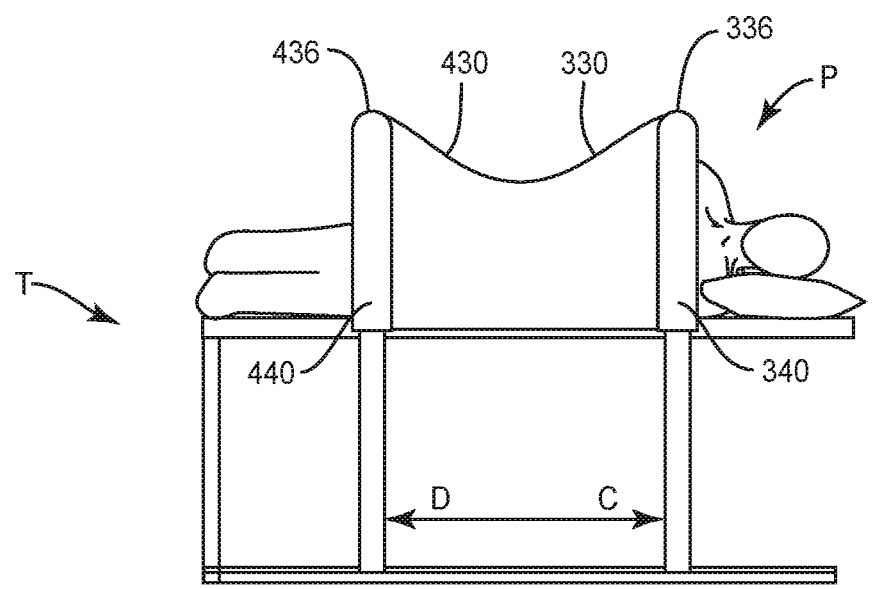
FIG. 11 is a side view of the components shown in FIG. 8.
Figure 12:
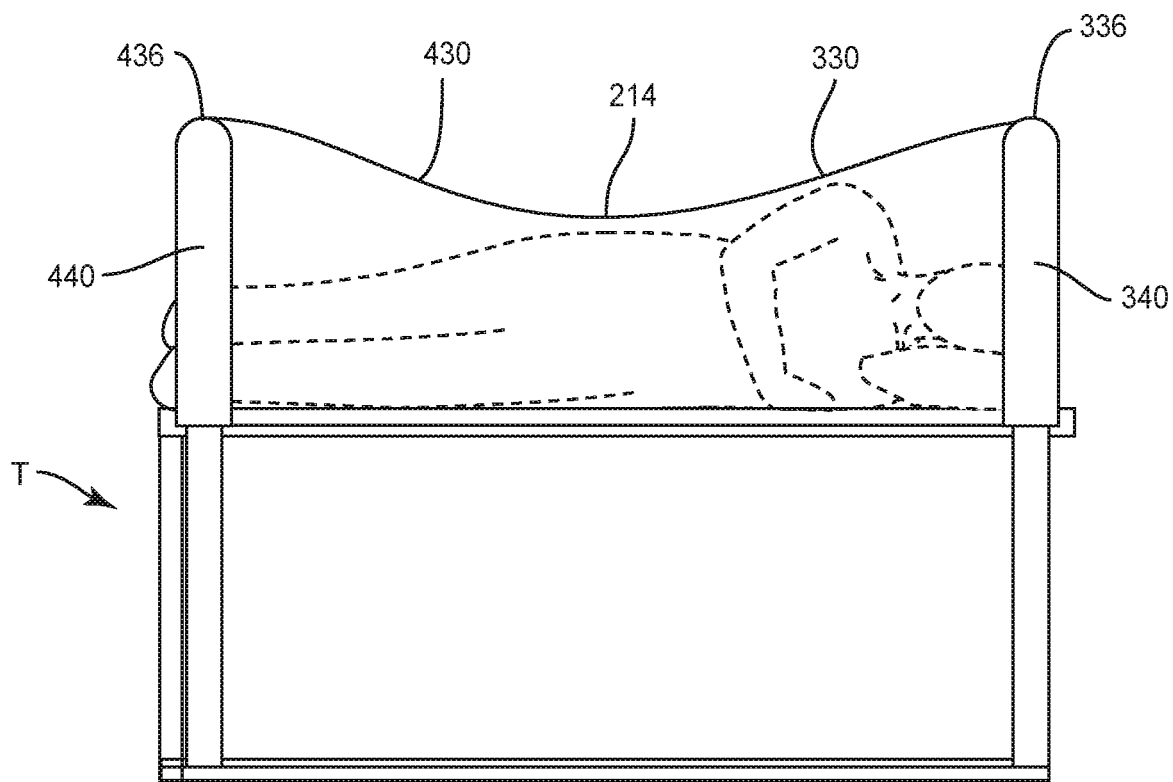
FIG. 12 is a side view of the components shown in FIG. 8.

Surgical drape 212 is configured to be disposed in a non-deployed orientation, as shown in FIG. 8, and manipulated, drawn, expanded and/or translated to a deployed orientation, as shown in FIGS. 9-12, for circumferential disposal about the body of patient P and/or to define a sterile region about the body of patient P. In the non-deployed orientation, drape 212 is disposed in a contracted, collapsed and/or compact configuration. For example, section 330 is wound, loaded, rotated and/or rolled to form a roll 336. Section 430 is wound, loaded, rotated and/or rolled to form a roll 436. Deployment loops 340, 440 are disposed about a mid-section of patient P, as shown in FIGS. 8 and 9. Seal 214 is disposed between roll 336 and roll 436, as shown in FIG. 10.

Roll 336 is mounted with deployment loop 340 and roll 436 is mounted with deployment loop 440 such that seal 214 is fixed with the body surface and draping 230 is drawn, expanded and/or translated relative to seal 214 in a telescoping configuration during deployment. Roll 336 is translated and/or guided along deployment loop 340 such that roll 336 facilitates circumferentially enclosing patient P and defining a sterile region. Roll 436 is translated and/or guided along deployment loop 440, similar to that described herein, such that roll 436 facilitates circumferentially enclosing patient P and defining the sterile region. In some embodiments, loop 340 and loop 440 are individually and/or separately slidable in a cranial direction and/or a caudal direction from a mid-section of patient P.

Seal 214 is positioned over the surgical site and adhered to the body surface of patient P. With seal 214 fixed with the body surface, deployment loop 340 is translated from the mid-section of patient P, in a direction shown by arrow C in FIGS. 10 and 11, relative to patient P and along surgical table T. In some embodiments, deployment loop 340 is translated in a cranial direction. Such translation of deployment loop 340 relative to patient P dispenses draping 330 from roll 336 away from seal 214 to draw, expand and/or translate draping 330 circumferentially about patient P. Deployment loop 440 is translated from the mid-section of patient P in a direction opposite to that of deployment loop 340, as shown by arrow D in FIGS. 10 and 11, relative to patient P and along surgical table T. In some embodiments, deployment loop 440 is translated in a caudal direction. Such translation of deployment loop 440 relative to patient P dispenses draping 430 from roll 436 away from seal 214 to draw, expand and/or translate draping 430 circumferentially about patient P. Surgical drape 212 maintains sterility within the sterile region as patient P is rotated in a range of 0 through 360 via surgical table T.

The surgeon can access the surgical site through seal 214, and the surgical procedure is performed including making incisions I1, I2, retracted openings, pathways and/or passageways in the tissue surfaces of patient P within the sterile region. In some embodiments, patient P is initially oriented in a lateral position or rotated by surgical table T from a prone position to a lateral position to provide surgical access via a lateral surgical approach to vertebral tissue within the sterile region. For example, a lateral lumbar interbody graft/cage insertion can be performed via the lateral surgical approach. In some embodiments, patient P is initially oriented in a prone position or rotated by surgical table T from a lateral position to a prone position to provide surgical access via the postero-lateral or posterior surgical approaches to vertebral tissue within the sterile region. For example, implantation of posterior instrumentation or constructs can be performed via postero-lateral or posterior surgical approaches. In some embodiments, rotation, repositioning and/or manipulation of patient P provides simultaneous access to the selected surgical approaches.

Upon completion of the procedure, the surgical instruments and non-implanted components are removed from the surgical site and the incisions, openings, pathways and/or passageways are closed. One or more of the components of surgical system 10 can be made of radiolucent materials such as polymers. Radiomarkers may be included for identification under x-ray, fluoroscopy, CT or other imaging techniques.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method of preparing a surgical site, the method comprising the steps of:
    disposing a preparation material with a selected surface of a patient body, the selected surface including a sterile region having a boundary;
    engaging a first applicator with the selected surface and moving the first applicator along a path from a first incision site of the selected surface to the boundary; and
    engaging a second applicator with the selected surface and moving the second applicator along a path from a second incision site of the selected surface to the boundary, the path of the first applicator intersecting the path of the second applicator,
    wherein the preparation material is an antiseptic fluid and the step of disposing includes spraying the antiseptic fluid on the selected surface,
    wherein at least one of the applicators include a sterile sponge;
    wherein the paths intersect at one half a distance between the incision sites, and
    wherein the paths intersect between the incisions on a lateral portion of a torso of the patient body.

2. A method as recited in claim 1, wherein the first incision site includes an anterior incision and the second incision site includes a posterior incision.

3. A method as recited in claim 1, wherein the path of the first applicator includes a plurality of arcuate swaths of increasing dimension.

4. A method as recited in claim 3, wherein the path of the second applicator includes a plurality of arcuate swaths of increasing dimension.

5. A method as recited in claim 1, wherein the path of the first applicator includes a continuous spiral configuration.

6. A method as recited in claim 5, wherein the path of the second applicator includes a continuous spiral configuration.

7. A method as recited in claim 1, wherein movement of the first applicator and/or the second applicator includes a continuous outward circular motion to the boundary.

8. A method as recited in claim 1, wherein the antiseptic fluid includes antimicrobial agents.

9. A method as recited in claim 1, further comprising the step of positioning the patient body right side down in a lateral decubitus position.

10. A method as recited in claim 1, wherein the first applicator is disposed with a center of an anterior incision and moved in a continuous spiral configuration along the first path to the boundary.

11. A method as recited in claim 10, wherein the second applicator is disposed with a center of a posterior incision and moved in a continuous spiral configuration along the second path to the boundary.

12. A method as recited in claim 11, wherein the paths intersect at one half a distance between the respective centers of the incisions.

13. A method as recited in claim 1, further comprising applying a surgical drape circumferentially around the patient body and rotating the patient body 360 degrees intra-operatively via a surgical table.

14. A method as recited in claim 1, further comprising deploying a surgical drape in a 360 degree configuration about the patient body, the surgical drape being attached to a deployment loop, the deployment loop being movably coupled to a surgical table.

15. A method of preparing a surgical site, the method comprising the steps of:

spraying an antiseptic fluid on to a selected surface of a patient body, the selected surface including a sterile region having a boundary;

engaging a first applicator with a center of a first incision and moving the first applicator in a continuous spiral configuration along a first path to the boundary; and engaging a second applicator with a center of a second incision and moving the second applicator in a continuous spiral configuration along a second path to the boundary, the path of the first applicator intersecting the path of the second applicator, wherein at least one of the applicators include a sterile sponge, wherein the first incision includes an anterior incision and the second incision includes a posterior incision, and wherein the paths intersect between the incisions on a lateral portion of a torso of the patient body.

16. A method of preparing a surgical site, the method comprising the steps of:

positioning a patient body right side down in a lateral decubitus position;

disposing a preparation material with a selected surface of the patient body, the selected surface including a sterile region having a boundary;

engaging a first applicator with the selected surface and moving the first applicator along a path from a center of an anterior incision of the selected surface to the boundary; and engaging a second applicator with the selected surface and moving the second applicator along a path from a center of a posterior incision of the selected surface to the boundary, the paths intersect at one half a distance between the respective centers of the incisions, wherein the preparation material is an antiseptic fluid and the step of disposing includes spraying the antiseptic fluid on the selected surface, wherein at least one of the applicators include a sterile sponge, wherein the paths intersect at one half a distance between the incision sites, and wherein the paths intersect between the incisions on a lateral portion of a torso of the patient body.

* * * * *